US00PP21078P2

(12) United States Plant Patent
Ichie

(10) Patent No.: US PP21,078 P2
(45) Date of Patent: Jun. 22, 2010

(54) ***HYDRANGEA* PLANT NAMED 'BLUE KNIGHT'**

(50) Latin Name: *Hydrangea macrophylla*
Varietal Denomination: Blue Knight

(76) Inventor: Toyokazu Ichie, 3-46 Hongou, Kakegawa-city, Shizuoka (JP) 436-0111

( * ) Notice: Subject to any disclaimer, the term of this patent is extended or adjusted under 35 U.S.C. 154(b) by 0 days.

(21) Appl. No.: 12/383,991

(22) Filed: Mar. 31, 2009

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent L Bell
(74) *Attorney, Agent, or Firm*—Penny J. Aguirre

(57) ABSTRACT

A new cultivar of *Hydrangea macrophylla* named 'Blue Knight' that is characterized by its early blooming habit, its ability to re-bloom on new growth after deadheading, its consistently well-formed, lacecap type inflorescences with large, double, rounded shaped sterile flowers that are light to dark blue under acidic conditions and bright pink under alkaline conditions, its deep green glossy foliage, and its strong stems that enable pot culture without staking.

2 Drawing Sheets

Botanical classification: *Hydrangea macrophylla.*
Varietal denomination: 'Blue Knight'.

BACKGROUND OF THE INVENTION

The present invention relates to a new and distinct cultivar of *Hydrangea macrophylla* and will be referred to hereafter by its cultivar name, 'Blue Knight'. 'Blue Knight' represents a new bigleaf *hydrangea*, a deciduous shrub grown for landscape use and for use as a potted plant.

'Blue Knight' was derived from an ongoing controlled breeding program that focuses on new cultivars of Bigleaf *Hydrangeas* for container and landscape use. 'Blue Knight' originated from a cross made in the Inventor's nursery in June 1999 in Shizuoka, Japan between two unpatented proprietary selections of *Hydrangea macrophylla*; the female parent designated as H3-67 and the male parent designated as H3-4.The new *Hydrangea* was selected as a unique single plant from the progeny of the cross in February 2006.

Asexual reproduction of the new cultivar was first accomplished by the Inventor using softwood stem cuttings in Shizuoka, Japan in May 2007. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Blue Knight' as a unique cultivar of *Hydrangea macrophylla.*

1. 'Blue Knight' is a strong bloomer and exhibits a re-blooming habit with inflorescences produced from early summer until fall with removal of spent blooms.
2. 'Blue Knight' exhibits consistently formed, large sized, lacecap type inflorescences with large double sterile flowers surrounding a mass of fertile flowers and some smaller double sterile flowers.
3. 'Blue Knight' exhibits inflorescences that are light to dark blue in color when grown under acidic soil conditions.

4. 'Blue Knight' exhibits a compact growth habit with strong stems that enable pot culture without the need for staking.
5. 'Blue Knight' exhibits dark green glossy foliage.
6. 'Blue Knight' is hardy at least in U.S.D.A. Zones 5 to 9.

'Blue Knight' differs from its female parent, H3-67, in having sterile flowers that are more round in shape and 20% larger in size. 'Blue Knight' differs from the male parent, H3-4, in having sterile flowers that are more round in shape, larger in size, and double rather than single. 'Blue Knight' can be compared to the cultivar 'Taube', which is similar in inflorescence shape and in having large sterile flowers that are a rich blue in color, however 'Taube' differs from 'Blue Knight' in having sterile flowers that are single and smaller in size. 'Blue Knight' can also be compared to the cultivar 'Jogasakei' (not patented), a cultivar which is similar for its dark green foliage and double sterile flowers, however the sterile flowers of 'Jogasaki' are more pink in color, even when grown under acidic conditions.

BRIEF DESCRIPTION OF THE DRAWINGS

The accompanying colored photographs illustrate the overall appearance and distinct characteristics of the new *Hydrangea* as grown outdoors in Shizuoka, Japan.

The photograph in FIG. 1 was taken of a three year-old plant of 'Blue Knight' as grown in a 3-gallon container and depicts the overall plant habit and inflorescence coloration as observed when grown under acidic soil conditions.

Figure 1:
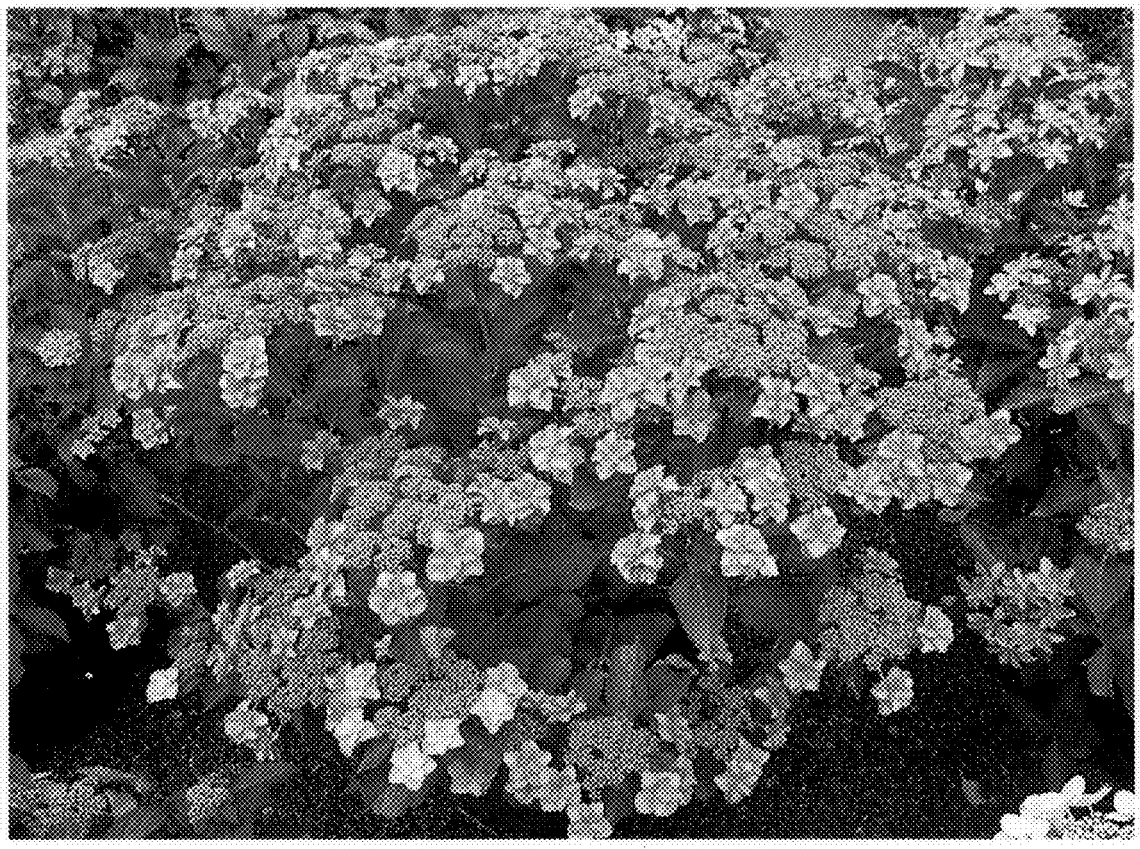
Figure 2:
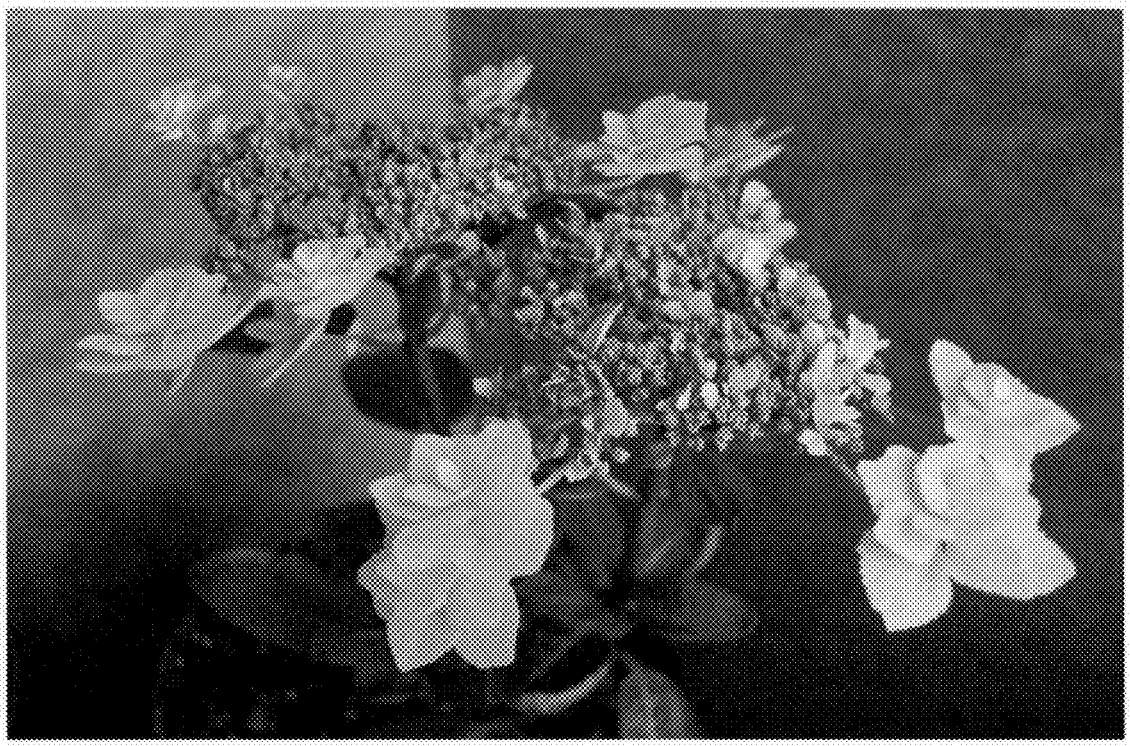

The photograph in FIG. 2 was taken of a one year-old plant of 'Blue Knight' as grown in a one-gallon container and illustrates a close-up view of an inflorescence when as grown under alkaline soil conditions.

The colors in the photographs may differ slightly from the color values cited in the detailed botanical description, which accurately describe the colors of the new *Hydrangea.*

BOTANICAL DESCRIPTION OF THE PLANT

The following is a detailed description of one year-old plants of 'Blue Knight' as grown outdoors in one-gallon containers in Shizuoka, Japan. The detailed inflorescence color data was taken from plants growing both under acidic conditions and alkaline conditions when differences exist. Phenotypic differences may be observed with variations in environmental, climatic, and cultural conditions. The color determination is in accordance with the 2007 R.H.S. Colour Chart of the Royal Horticultural Society, London, England, except where general color terms of ordinary dictionary significance are used.

General description:

*Blooming period.*—Reblooming from June until frost from with removal of spent blooms in Shizuoka, Japan.

*Plant habit.*—Broadly upright, deciduous shrub, strong stems.

*Height and spread.*—Reaches about 60 cm in height and width on three-year-old plants grown in a 3-gallon container.

*Hardiness.*—At least to U.S.D.A. Zones 5 to 9.

*Diseases resistance.*—No susceptibility or resistance to diseases known to effect *H. macrophylla* has been observed.

*Root description.*—Fine.

Growth and propagation:

*Propagation.*—Softwood stem cuttings.

*Growth rate and vigor.*—Moderate.

Stem description:

*Stem shape.*—Round, solid.

*Stem strength.*—Very strong.

*Stem color.*—New growth; 144A with lenticels 177A, woody; blend of 199C and 199D.

*Stem size.*—Average of 20.6 cm (to base of inflorescence), average of 5 mm in width.

*Stem surface.*—Glabrous, slightly glossy, sparsely covered with lenticels; about 4 per square cm and average of 1.5 mm in length and 0.5 mm width, stem becomes bark-like with age.

*Internode length.*—Average of 6 cm.

*Branching.*—Lateral branching is determined by pinching; 2 stems develop per pinched node.

Foliage description:

*Leaf shape.*—Primarily elliptic.

*Leaf arrangement.*—Opposite.

*Leaf division.*—Simple.

*Leaf number.*—Average of 12 (6 pairs) per lateral branch 17 cm in length.

*Leaf base.*—Cuneate.

*Leaf apex.*—Cuspidate.

*Leaf margins.*—Serrated, average of 11 per side on a mature leaf 10 cm in length.

*Leaf venation.*—Penninerved, recessed on upper surface, color 138C on upper surface and 144D on lower surface.

*Leaf size.*—Matures to an average of 9 cm in length and 6 cm in width.

*Leaf attachment.*—Petiolate.

*Leaf surface.*—Glabrous and glossy on upper surface, glabrous and finely puberulent on lower surface.

*Leaf color.*—Young foliage upper surface; 138A, young foliage lower surface; between 144A, mature foliage upper surface; between 137A and 137NA, mature foliage lower surface; 138B.

*Petioles.*—Average of 1.3 cm in length and 3.5 mm in width, 144B to 144C in color, glabrous surface.

Inflorescence description:

*Inflorescence type.*—Terminal compound corymb, lacecap in form comprised of a center region of fertile (pistillate) flowers surrounded by an outer ring of large double sterile flowers.

*Lastingness of inflorescence.*—Persistent but color is retained for about 4 weeks.

*Inflorescence number.*—One per lateral or sublateral stem if pinched.

*Inflorescence size.*—Average of 8 cm in depth and 20 cm in diameter.

*Flower number.*—Average of 5 sterile flowers and 350 fertile flowers.

*Flower fragrance.*—None.

*Flower aspect.*—Fertile flowers upright, sterile flowers are upright on horizontal pedicels.

*Flower size.*—Sterile flowers; average of 5 cm in diameter and 2.5 cm in depth, 5 mm in diameter and depth.

*Flower buds.*—Sterile flowers; average of 6 mm in length and 4.5mm in width prior to opening, ovate in shape, 144D in color prior to opening, fertile flowers; average of 4 mm in width and diameter, globose in shape, 63C in color.

*Peduncles.*—Sterile flowers; Strong, average of 2.5 cm in length and 2.5 mm in width, 144A in color with lenticels of 177A, glabrous surface.

*Pedicels.*—Sterile flowers; held horizontally, average of 4.2 cm in length and 1.5 mm in width, color 63C under alkaline conditions and 97C under acidic conditions, fertile flowers; average of 4 mm in length and 0.5 mm in width, color 144D becoming flushed with 63D and 97C under acidic conditions, surface is glabrous on all flowers.

*Petals.*—3, present on fertile flowers only, rotate in arrangement, elliptic in shape, entire margin, rounded apex, truncate base, average of 5.5 mm in length and 3 mm in width, surface is glabrous and dull on both surfaces, color of upper and lower surface on open flower is 63C when open under alkaline conditions and 97A to 97B under acidic conditions.

*Sepals.*—Sterile flowers; average of 16, ovate in shape, range of 1.2 to 2.5 cm in length and 0.8 to 2.3 cm in width (outer sepals are larger), broadly acute to rounded apex, cuneate base, glabrous surface on upper and lower surface, serrated margins, color under alkaline conditions: color when flower opens upper and lower surface; 73D with center sepals 150D, color when flower is fully open upper surface; 63D, color when flower is fully open lower surface; blend of 73D with veins 73C, color under acidic conditions: color when flower opens upper and lower surface; a blend of 98B, 98C and 97A to 97D, color when flower is fully open upper and lower surface; blend of 85C, 97B to 97D, fertile flowers; 5, obovate in shape, entire margin, rounded apex, truncate base, average of 2 mm in length and 1 mm in width, surface is glabrous and dull on both surfaces, color of upper and lower surface on open flower is a blend of 63D and 150D under alkaline conditions and a blend of 97C and 150D under acidic conditions.

*Eye* (*sterile flowers*).—150D changing to 63D under alkaline conditions and 150D changing to 97A under acidic conditions when fully open.

Reproductive organs: (Fertile flowers, pistillate):

*Stamens.None.*—None observed, astemonous.

*Pistils.*—Average of 3, average of 3 mm in length and 0.5 mm in width, stigma is club-shaped and 64A and 1 mm in diameter, in color, style is an average of 2 mm in length and blend of 63D and 150D in color, ovary is inferior and about 145D in color.

*Fruit and seed.*—Has not been observed under the conditions tested to date.

It is claimed:

1. A new and distinct cultivar of *Hydrangea* plant named 'Blue Knight' substantially as herein illustrated and described.

* * * * *